(12) United States Patent
Mines et al.

(10) Patent No.: US 10,596,009 B2
(45) Date of Patent: Mar. 24, 2020

(54) KNEE AUGMENT

(71) Applicant: Smith & Nephew, Inc., Memphis, TN (US)

(72) Inventors: Angela Black Mines, Mason, TN (US); Michael Cole, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/833,808

(22) Filed: Mar. 15, 2013

(65) Prior Publication Data

US 2014/0277528 A1 Sep. 18, 2014

(51) Int. Cl.
*A61F 2/30* (2006.01)
*A61F 2/38* (2006.01)

(52) U.S. Cl.
CPC .......... *A61F 2/389* (2013.01); *A61F 2/30734* (2013.01); *A61F 2/3859* (2013.01); *A61F 2002/30331* (2013.01); *A61F 2002/30736* (2013.01)

(58) Field of Classification Search
CPC .... A61F 2/389; A61F 2/38; A61F 2002/2835; A61F 2/28; A61F 2/64; A61F 5/0106
See application file for complete search history.

(56) References Cited

U.S. PATENT DOCUMENTS

| | | | | |
|---|---|---|---|---|
| 4,790,852 A | * | 12/1988 | Noiles | A61B 17/175 623/23.46 |
| 4,944,757 A | * | 7/1990 | Martinez | A61F 2/389 623/20.15 |
| 5,019,103 A | * | 5/1991 | Van Zile | A61F 2/30734 623/20.34 |
| 5,152,797 A | * | 10/1992 | Luckman | A61F 2/30734 623/20.16 |
| 5,658,341 A | * | 8/1997 | Delfosse | A61F 2/38 623/20.32 |
| 5,702,464 A | * | 12/1997 | Lackey | A61F 2/4684 623/20.32 |
| 5,782,920 A | * | 7/1998 | Colleran | 623/20.34 |

(Continued)

FOREIGN PATENT DOCUMENTS

WO 2012162180 A1 11/2012

OTHER PUBLICATIONS

International Search Report and Written Opinion for International Application No. PCT/US2014/022617, dated Jul. 3, 2014.

(Continued)

*Primary Examiner* — Ann Schillinger

(57) ABSTRACT

A knee prosthesis kit includes an implant and an augment. The implant has a base and a stem extending from the base, and the augment has a base and a conical, cylindrical, or anatomic portion extending from the base. The augment base has at least two openings for receiving fasteners for securing the knee augment to the implant. The portion and the base define a bore for receipt of the implant post. A coupler includes a mating portion for receipt in a bore of an implant post, and a cone-shaped portion extending from the mating portion. A method of providing fixation of knee implants includes securing an augment to an implant and positioning a conical, cylindrical, or anatomic portion of the augment within the intramedullary canal of the tibia or femur.

35 Claims, 11 Drawing Sheets

(56) References Cited

U.S. PATENT DOCUMENTS

| | | | |
|---|---|---|---|
| 5,800,552 A * | 9/1998 | Forte | A61F 2/3845 |
| | | | 623/20.27 |
| 5,879,391 A * | 3/1999 | Slamin | A61F 2/38 |
| | | | 623/20.15 |
| 6,953,479 B2 | 10/2005 | Carson et al. | |
| 7,357,817 B2 | 4/2008 | D Alessio et al. | |
| 7,842,093 B2 * | 11/2010 | Peters et al. | 623/20.15 |
| 2004/0049286 A1 | 3/2004 | German et al. | |
| 2004/0162619 A1 | 8/2004 | Blaylock et al. | |
| 2007/0088443 A1 | 4/2007 | Hanssen | |
| 2007/0179627 A1 * | 8/2007 | Gustilo | A61F 2/30734 |
| | | | 623/20.15 |
| 2009/0149964 A1 * | 6/2009 | May | A61B 17/155 |
| | | | 623/20.15 |
| 2010/0076565 A1 | 3/2010 | Thomas | |
| 2011/0112651 A1 | 5/2011 | Blaylock et al. | |
| 2012/0310361 A1 * | 12/2012 | Zubok | A61F 2/30734 |
| | | | 623/20.32 |

OTHER PUBLICATIONS

European Examination Report; European Patent Office; European Patent Application No. 14768856.8; dated Jan. 2, 2019; 4 pages.

\* cited by examiner

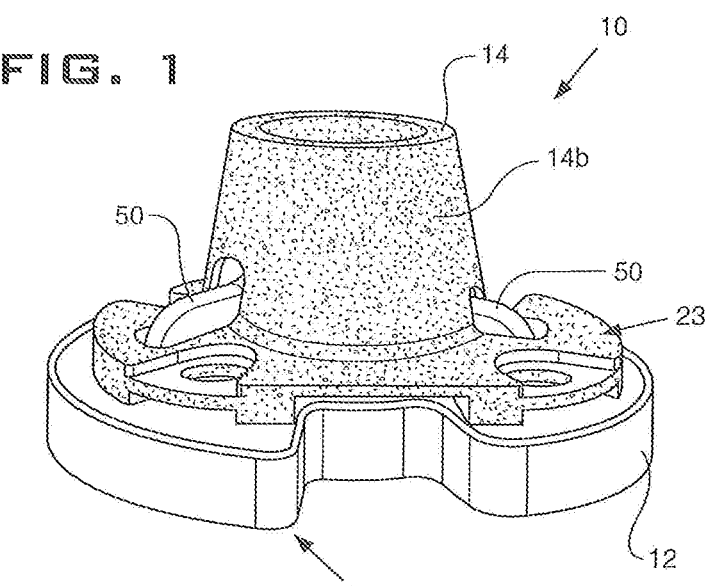
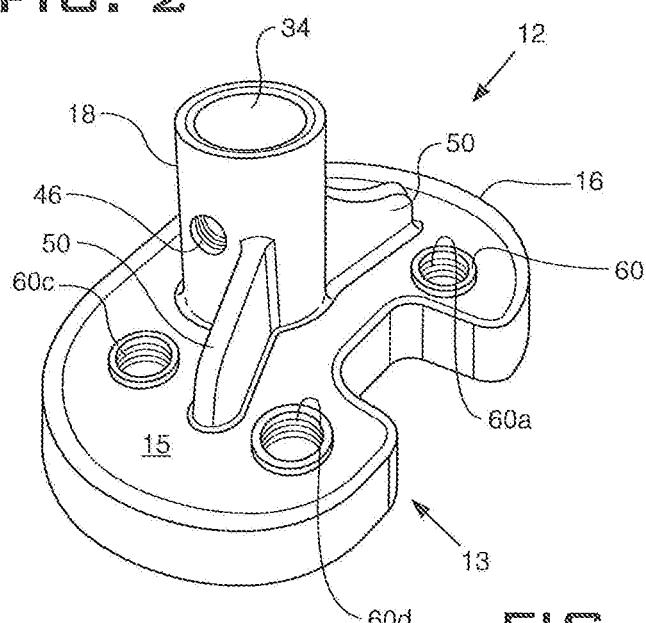
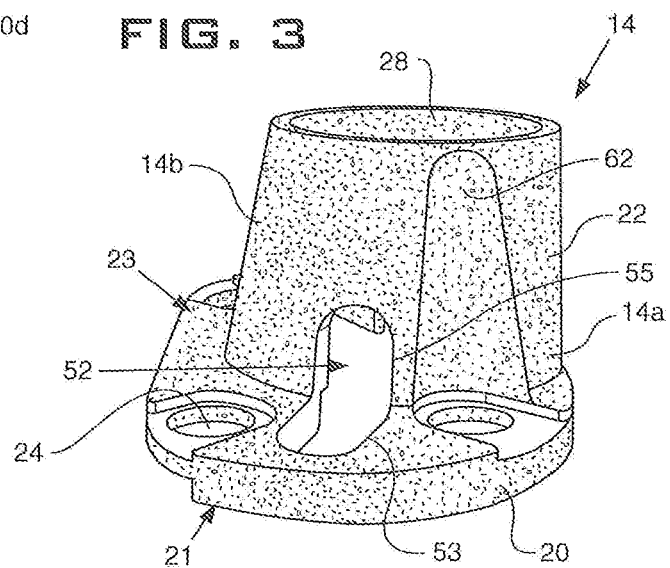

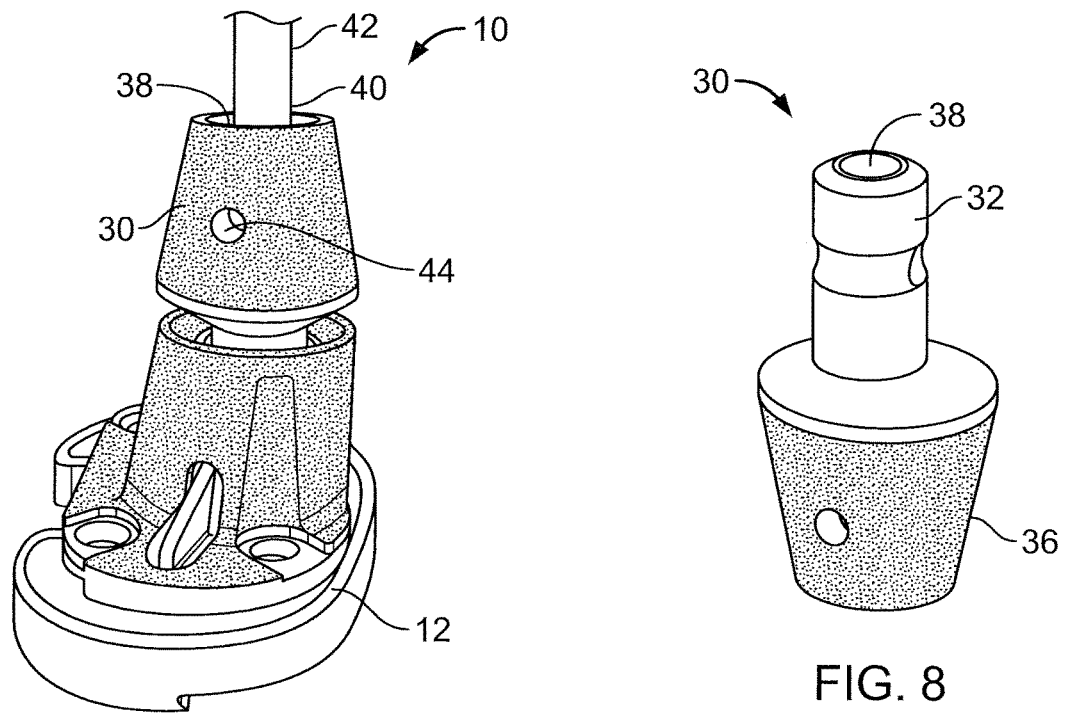
FIG. 7
FIG. 8
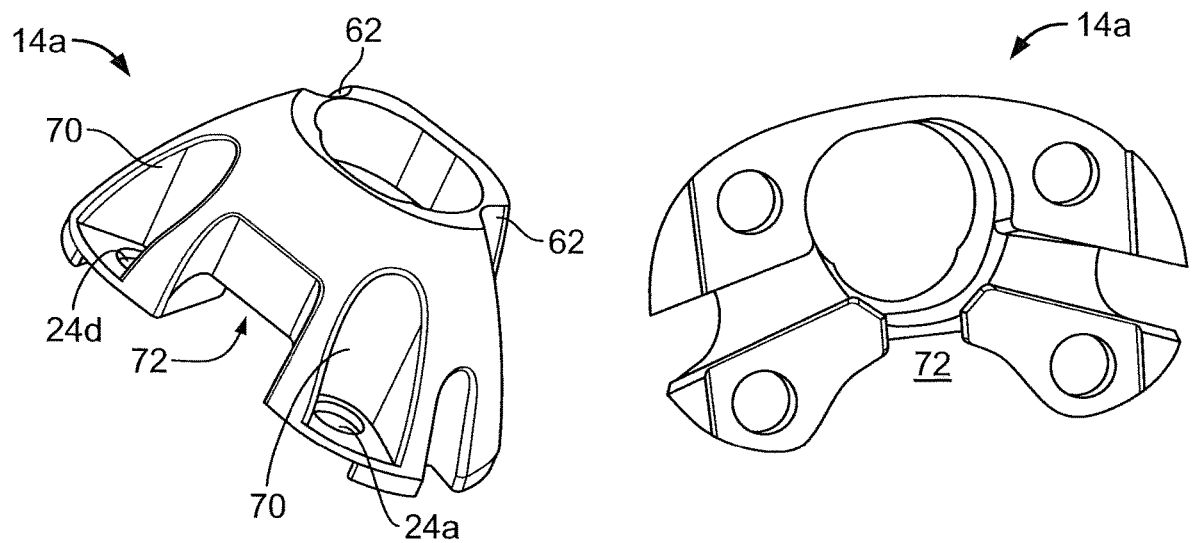
FIG. 9A
FIG. 9B

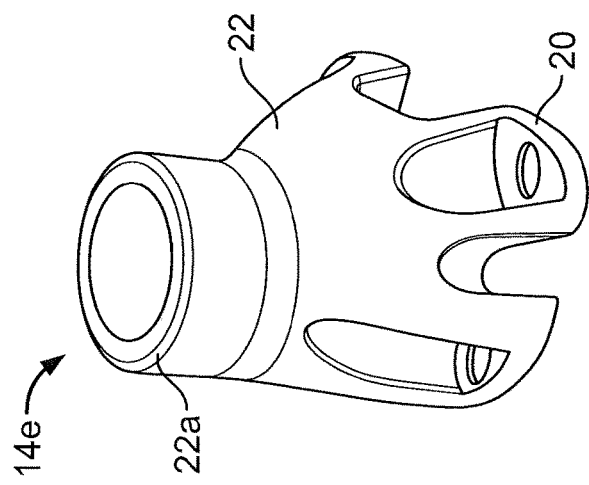
FIG. 12
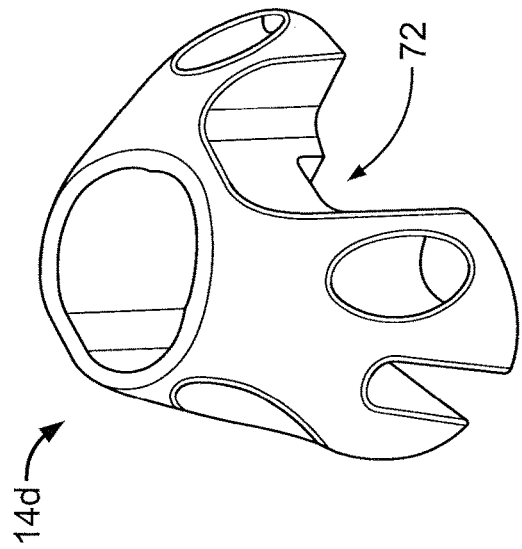
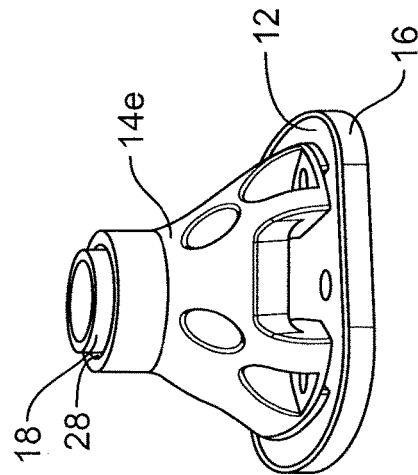
FIG. 13
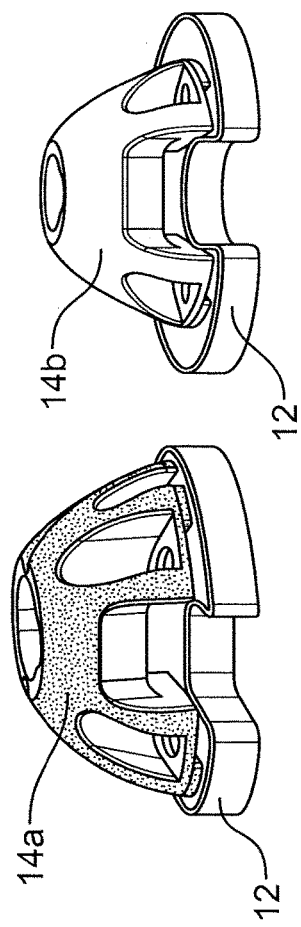
FIG. 14

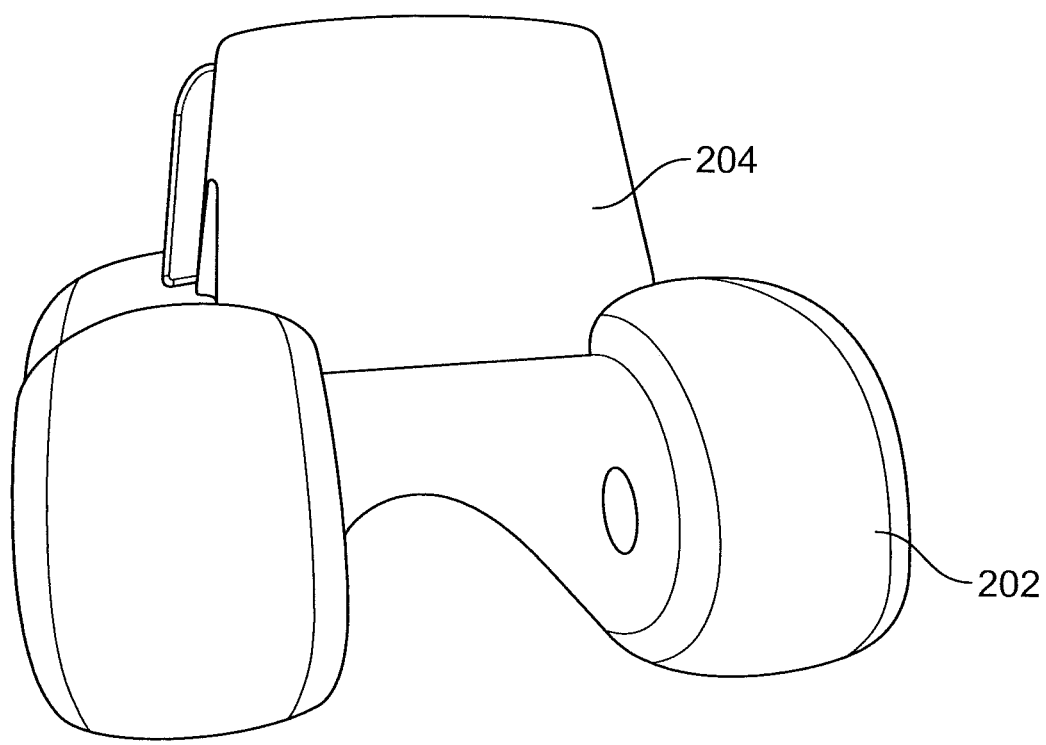
FIG. 27A
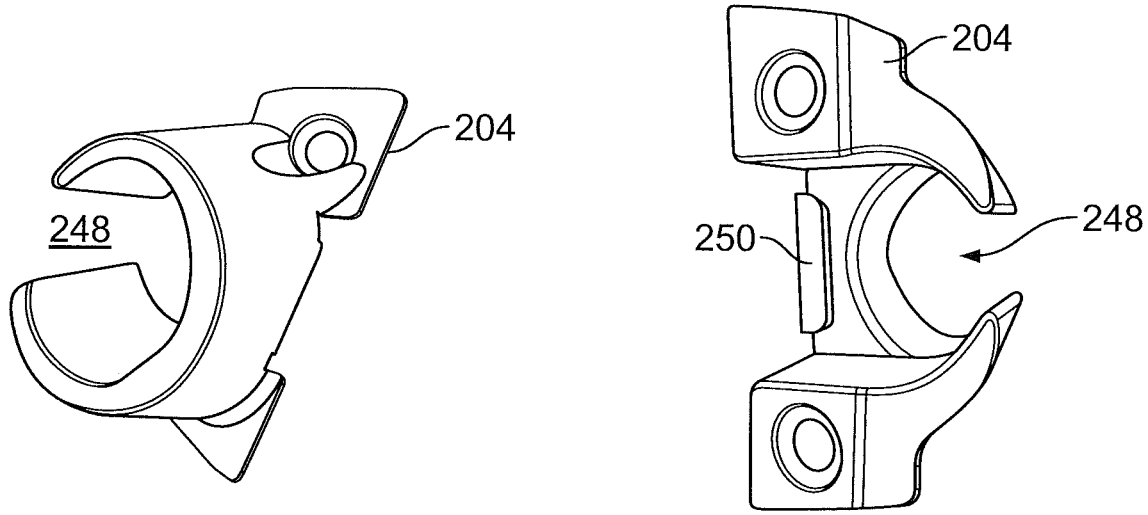
FIG. 27B
FIG. 27C

KNEE AUGMENT

TECHNICAL FIELD

This invention relates to knee augments and knee prosthesis kits.

BACKGROUND

Prosthesis including femoral and tibia implants are used in total knee arthroplasty and total knee revision surgeries. The prosthesis may include an adapter that replaces a portion of the bone and a coupling sleeve having an offset coupling axis.

SUMMARY

A knee prosthesis kit includes components designed to optimize fixation of tibia and femoral implants, especially in the case of revision surgeries and/or oncology procedures, to improve fixation of the metaphyseal junction. In revision and primary procedures where the bone quality and ligamentous attachments are compromised, additional implant stability aids in ensuring adequate fixation and promotes good function of the implant. The kit includes cone-shaped members that are fixed to the implants in a secured, fixed position. The cone-shaped members improve the rotational stability of the femur and tibia. The cone-shaped members extend proximally (for use with a femoral implant) or distally (for use with a tibia implant) from the implant at a variety of lengths to accommodate a multitude of bone deformities.

A knee prosthesis kit includes an implant and an augment. The implant has a base and a stem extending from the base, and the augment has a base and a conical, anatomic, or cylindrical portion extending from the base.

Implementations of this aspect may include one or more of the following features.

The augment base has at least two openings, for example, four openings, for receiving fasteners for securing the augment to the implant base. The conical, cylindrical, or anatomic portion and the augment base define a bore for receipt of the implant stem. The augment is sized relative to the implant such that when the augment is secured to the implant base, the stem extends out of the bore. The height of the augment does not restrict the offset coupling ability of the base implant with the stem. The implant includes wings extending from the post, and the augment defines clearance space in at least one of the base and the conical, cylindrical, or anatomic portion arranged to receive the wings.

The implant is a first implant or a second implant, and the first implant is smaller than the second the implant. A first two of the augment openings are spaced apart to match the smaller size implant, and the other two of the augment openings are spaced apart a different amount from the first two openings to match the larger size implant.

The implant base includes at least two openings for receiving fasteners. The implant base openings and the augment base openings are aligned when the augment is fastened to the implant. The implant base openings do not extend all the way through the implant base.

The augment includes a locking feature, for example, a tail, configured to snap into the implant to provide a friction fit between the augment and the implant. The outer surface of at least the conical, cylindrical, or anatomic portion is sintered, stepped, ribbed, or splined. The augment includes a cylindrical portion extending from a cone-shaped portion. The conical, cylindrical, or anatomic portion defines slots aligned with the at least two augment base openings that provide clearance for the fasteners.

The kit includes an offset coupler having a mating portion for receipt in a bore of the implant stem and a cone-shaped portion extending from the mating portion. The cone-shaped portion defines a bore for receipt of an intramedullary rod, and a central axis of the bore is offset from a central axis of the mating portion. The offset coupler is configured to be secured in the bore of the implant stem by a taper lock. The kit includes the intramedullary rod. The offset coupler bore is configured to secure the intramedullary rod by a taper lock. The implant is a tibial plate or a femoral implant. The kit includes a wedge.

According to another aspect, a knee augment includes a base having at least two openings for receiving fasteners for securing the knee augment to an implant, and a conical, cylindrical, or anatomic portion extending from the base. The portion and the base define a bore for receipt of a stem of the implant.

Implementations of this aspect may include one or more of the following features.

The knee augment defines clearance openings in at least one of the base and the conical, cylindrical, or anatomic portion arranged to receive wings extending from the stem of the implant. The base defines four openings for receiving fasteners. A first two of the openings are spaced apart to match a smaller size implant, and the other two of the openings are spaced apart a different amount from the first two openings to match a larger size implant. The knee augment includes a locking feature configured to snap into the implant to provide a friction fit between the knee augment and the implant. An outer surface of at least the conical, cylindrical, or anatomic portion is sintered, stepped, ribbed, or splined. The knee augment includes a cylindrical portion extending from a cone-shaped portion.

According to another aspect, a coupler includes a mating portion for receipt in a bore of an implant post, and a cone-shaped portion extending from the mating portion. The cone-shaped portion defines a bore for receipt of an intramedullary rod. A central axis of the bore is offset from a central axis of the mating portion.

Implementations of this aspect may include an outer surface of the cone-shaped portion being sintered, stepped, ribbed, or splined.

According to another aspect, a method of providing fixation of knee implants includes securing an augment to an implant, and positioning a conical, cylindrical, or anatomic portion of the augment within the intramedullary canal of the tibia or femur.

Implementations of this aspect may include one or more of the following features.

The augment is secured to the implant by placing a least two fasteners through openings in the augment and the implant. The augment defines a bore for receipt of a stem of the implant. The augment to secured to a tibial tray. The augment is secured to a femoral implant.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is an isometric view of a knee prosthesis kit including a tibial tray and an augment.

FIG. 2 is an isometric view of the tibial tray.

FIGS. 3 and 4 are side and isometric views of the augment.

FIG. 7 is a side view of the knee prosthesis kit including a coupler.

FIG. 8 is a side view of the coupler.

FIGS. 9A-16 illustrate additional augments.

FIGS. 25A-27C illustrate additional augments used with femoral implants.

DETAILED DESCRIPTION

Figure 4:
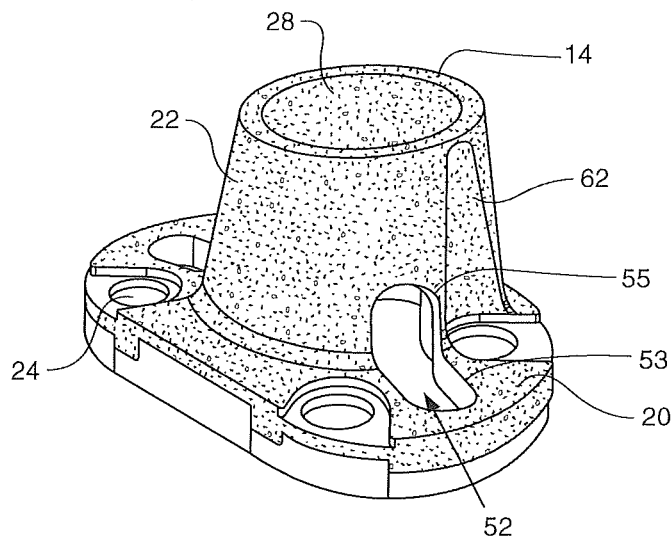

Referring to FIGS. 1-4, a knee prosthesis kit 10 includes an implant 12 and an augment 14. The implant 12, for example, a tibial plate, includes a base 16 and a stem 18 extending from the base 16. The augment 14 has an anterior side 14a and a posterior side 14b, and includes a base 20 and a conical, cylindrical, or anatomic portion, here a cone-shaped portion 22 is shown, extending from the base 20. To fix the augment 14 to the implant 12 in a secured, fixed position, the augment base 20 includes at least two openings 24, here four openings 24a-24d are shown, for receiving fasteners 26 (FIG. 6) for securing the augment 14 to the implant base 16. The cone-shaped portion 22 of the augment 14 and the augment base 20 define a bore 28 sized to receive the implant stem 18. The implant base 16 includes superior side 13 and an inferior surface 15. The augment base 20 has an implant contacting surface 21 and a bone contacting surface 23. As depicted in FIG. 2, the wings 50 are generally planar, fin-like or wall-shaped, and extend from the stem 18 and from the inferior surface 15 to form a structural rib or brace.

The cone-shaped portion 22 of the augment 14 is designed to optimize fixation of the implant 12, especially in the case of revision surgeries and/or oncology procedures, to improve fixation of the metaphyseal junction. In revision and primary procedures where the bone quality and ligamentous attachments are compromised, the cone-shaped portion 22 provides additional implant stability by filling the void left by bone deformities thus aiding in ensuring adequate fixation of the implant to the tibia, promoting good function of the implant, and improving the rotational stability of the tibia.

Figure 5:
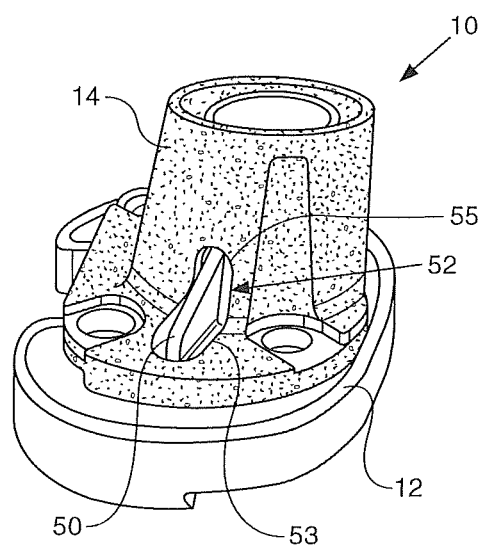
FIG. 5 is a side view of the tibial tray and augment.

Referring also to FIG. 5, the implant 12 includes wings 50 extending from the stem 18, and the augment 14 has clearance spaces 52 defined in the base 20 and the cone-shaped portion 22 that are arranged to receive the wings 50. The clearance space 52 has a first portion 53 in the base 20 and a second portion 55 in the cone-shaped portion 22.

Figure 6:
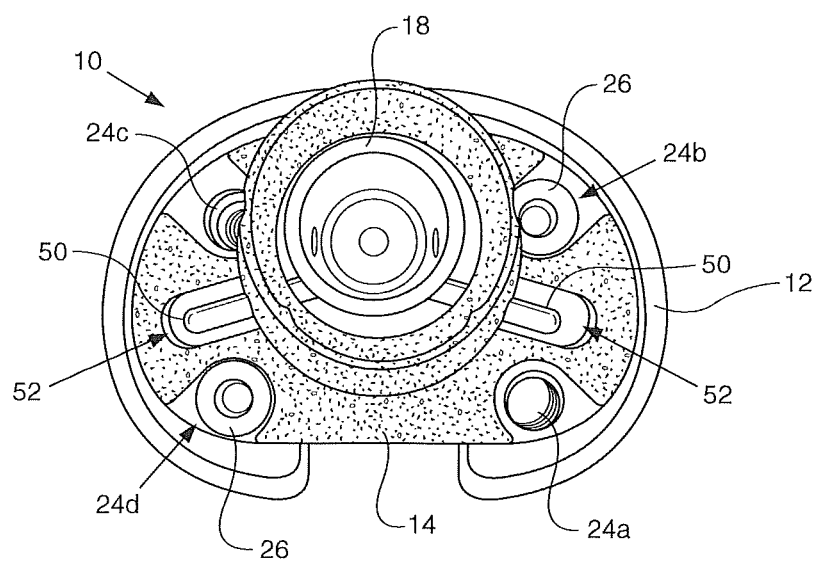
FIG. 6 is a top view of the tibial tray and augment.
Figure 10A:
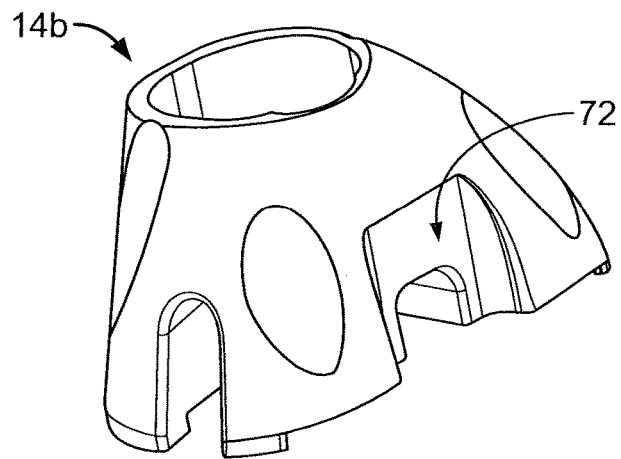
Figure 10B:
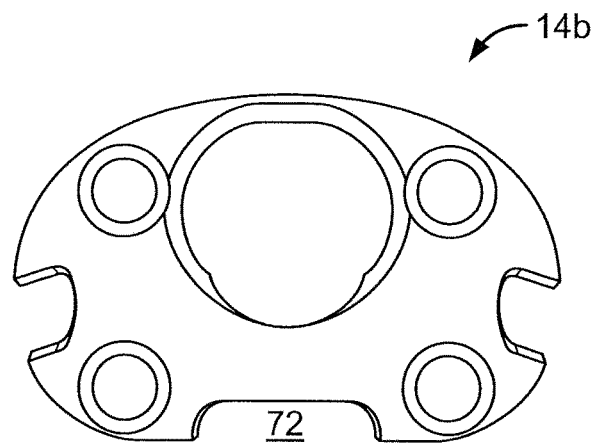
Figure 11A:
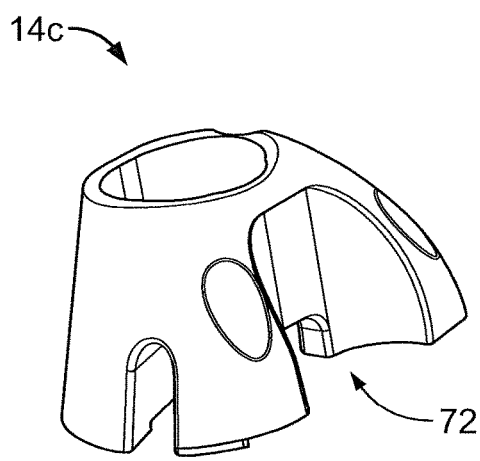
Figure 11B:
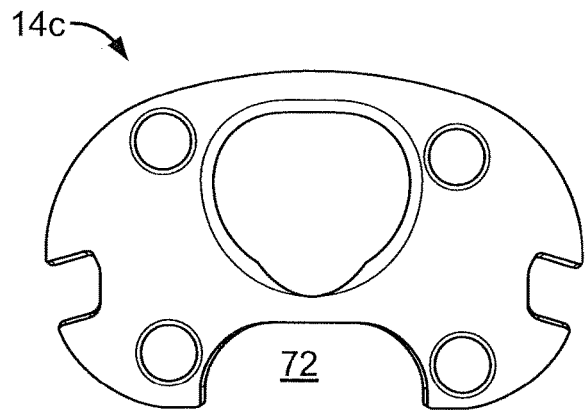

Referring to FIGS. 2 and 6, to secure the augment 14 to the implant 10 using fasteners 26, the implant base 16 has at least two openings 60, here four openings 60a-60d are shown (opening 60b being hidden in FIG. 2), that align with openings 24a-24d, respectively, when the augment 14 is positioned on the implant 12 with the implant wings 50 received in clearance spaces 52. The openings 60a-60d do not extend all the way through the base 16 such that the fasteners 26 located in openings 24a-24d and 60a-60d do not extend into the joint space and such that any wear debris cannot migrate through the implant to potentially cause osteolysis.

The augment 14 can be used with different sized implants 12 by varying the distance between opposing cross-openings 24a, 24c and opposing cross-openings 24b, 24d. A smaller spacing between openings 24a, 24c can accommodate a smaller implant 12, while a larger spacing between openings 24b, 24d can accommodate a larger implant 12. In such a configuration, two fasteners 26 would be placed in opposing openings that align with the implant openings to secure the augment 14 to the implant 12. Alternatively, the spacing between the pairs of opposing openings can be the same such that the augment 14 has a dedicated size and four fasteners 26 are used to secure the augment 14 to the implant 12. The augment 14 can include only two opposing openings 24 such that a dedicated size augment 14 is attached to the implant using two fasteners 26.

To provide access for insertion of the fasteners 26 into the augment openings 24b and 24c, the cone-shaped portion 22 of the augment 14 has slots 62 aligned with the augment base openings 24b and 24c that provide clearance for the fasteners. The outer surface of the cone-shaped portion 22 can be sintered, stepped, ribbed, or splined to aid in bone purchase.

Referring to FIGS. 7 and 8, additional components can be attached to the implant 12 via the stem 18. For example, the kit 10 can further include a standard coupler and/or an offset coupler 30 having a mating portion 32 for receipt in a bore 34 (FIG. 2) of the implant stem 18. The standard coupler or the offset coupler 30 can include in some implementations a cone-shaped portion 36 extending from the mating portion 32. The cone-shaped portion 36 defines a bore 38 for receipt of a mating end 40 of an intramedullary rod 42 of the kit 10. In the offset coupler configuration, the bore 38 has a central axis that is offset from a central axis of the mating portion 32, by, for example, 2 mm, 4 mm, or 6 mm. The kit 10 can include multiple offset couplers with different offsets.

The mating portion 32 of the coupler and the bore 34 of the implant stem 18 can be tapered such that the coupler 30 can be secured to the implant 12 by a taper lock. Likewise, the bore 38 of the coupler 30 and the mating end 40 of the intramedullary rod 42 can be tapered to provide a taper lock therebetween. The cone-shaped portion 36 can define a threaded through hole 44 extending through the wall of the coupler for receipt of a locking screw. The locking screw extends to a threaded hole 46 (FIG. 2) in the stem 18 to aid in securing the coupler to the implant. The outer surface of the coupler can be sintered, stepped, ribbed, or splined to aid in bone purchase.

Referring to FIGS. 9A-12, alternative augments 14a-14d that generally correspond to augment 14 described above, vary in the curvature of the outer surface of the cone-shaped portion 36. The outer surfaces of the augments 14a-14d have a more rounded contour than augment 14 that extends beyond the openings 24a and 24d. The augments 14a-14d therefore define additional posterior slots 70 for receiving fasteners. Due to the more rounded contour, each of the augments 14a-14d also defines a posterior facing notch 72 having a profile which matches the profile of an underlying implant 12. Each of the augments 14a-14d includes a base and a cone-shaped portion, as described above. The augments can vary in shape and length to accommodate different bone deformities and a variety of tibia base plate implants.

Figure 15:
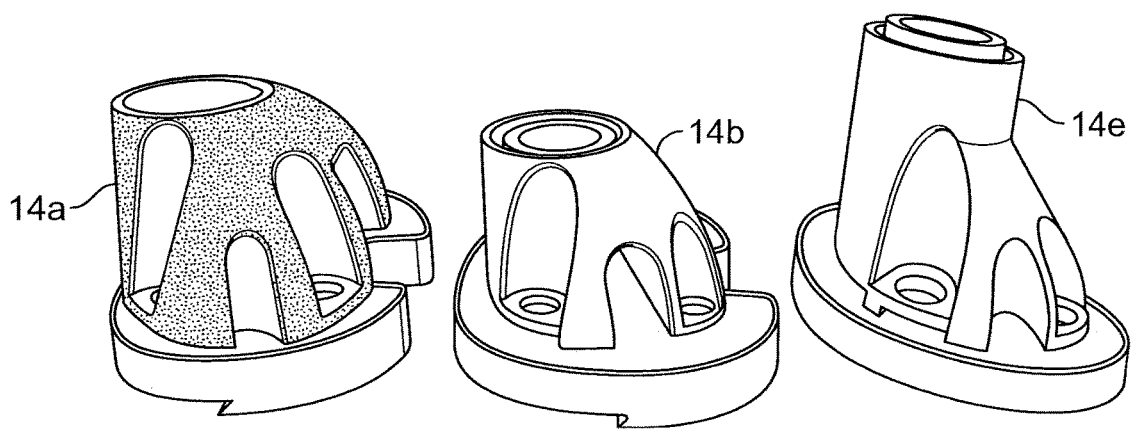
Figure 16:
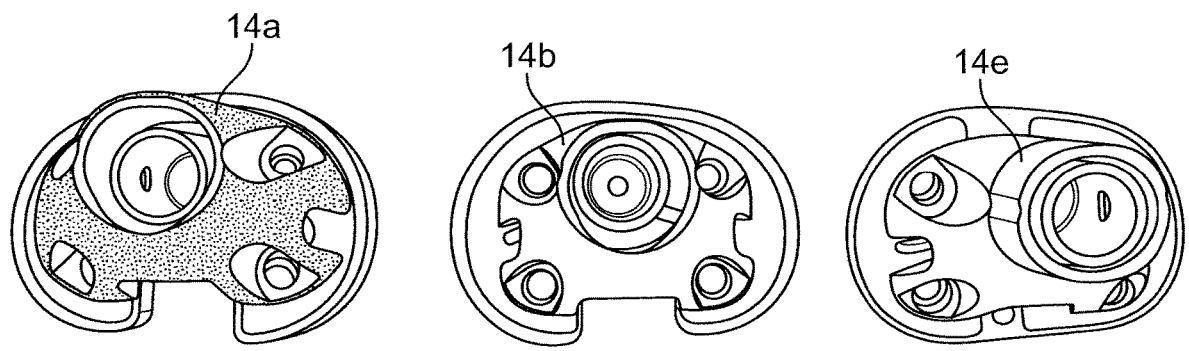
Figure 17:
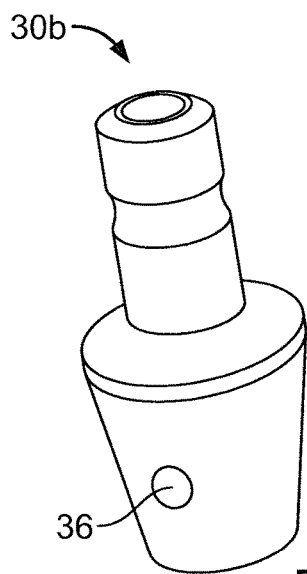
FIG. 17-20 illustrate additional couplers.
Figure 18:
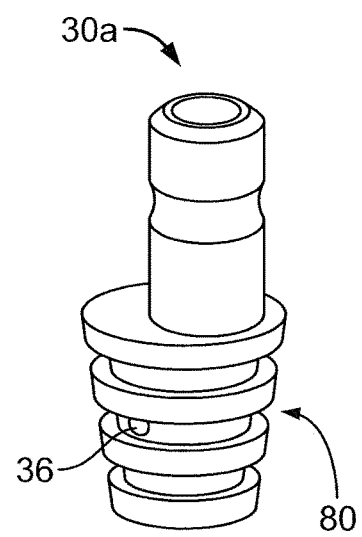
Figure 19:
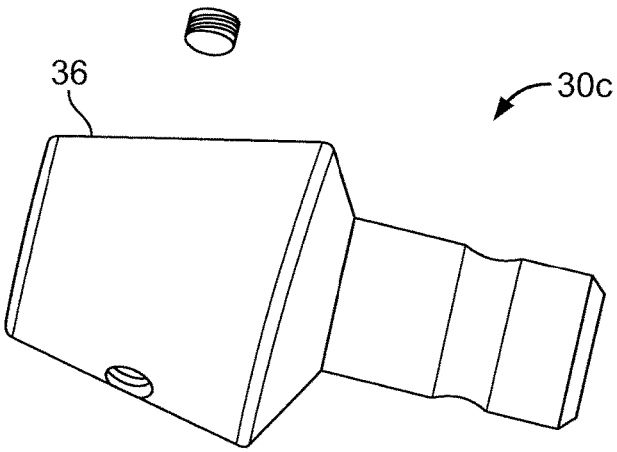
Figure 20:
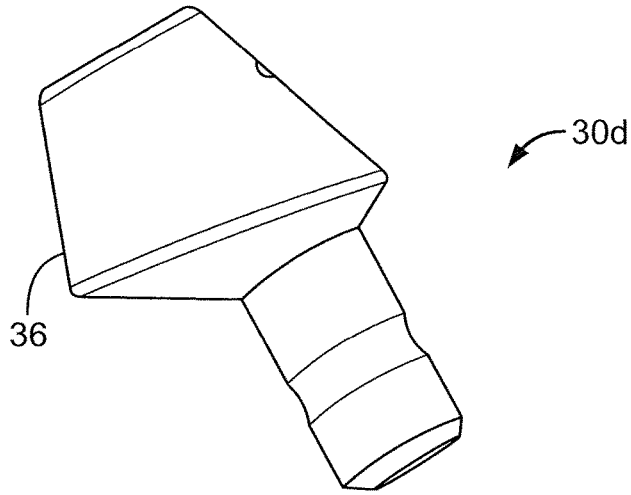

Referring to FIG. 13, in an additional implementation, an augment 14e includes a base 20, a cone-shaped portion 22, and a cylindrical portion 22a extending from the cone-shaped portion 22. Various views of augments 14a, 14b and 14e attached to implants 12 are shown in FIGS. 14-16, which illustrate how the augments vary in shape to accommodate different implants 12 and different bone deformities. As can be seen in FIGS. 14 and 15, the augment 14e is sized relative to the implant 12 such that when the augment 14e is secured to the implant base 16, the stem 18 extends out of the bore 28 of the augment. This relative sizing facilitates the attachment of additional components to the implant 12 via the stem 18.

Figure 21:
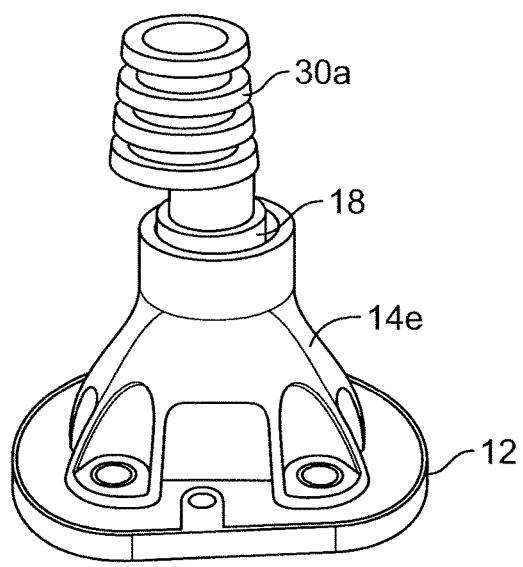
FIG. 21 is an isometric view a knee prosthesis kit including a coupler.

Referring to FIGS. 17-20, alternative offset couplers 30a-30d generally correspond to offset coupler 30 described above, but can include ribs 80 to add in bone purchase, and can include cone-shaped portions 36 of varying shape and/or concave or convex radial features of varying shape to accommodate different bone defects. FIG. 21 illustrates the augment 14e attached to an implant 12 with the offset coupler 30a received by the stem 18.

Figure 22:
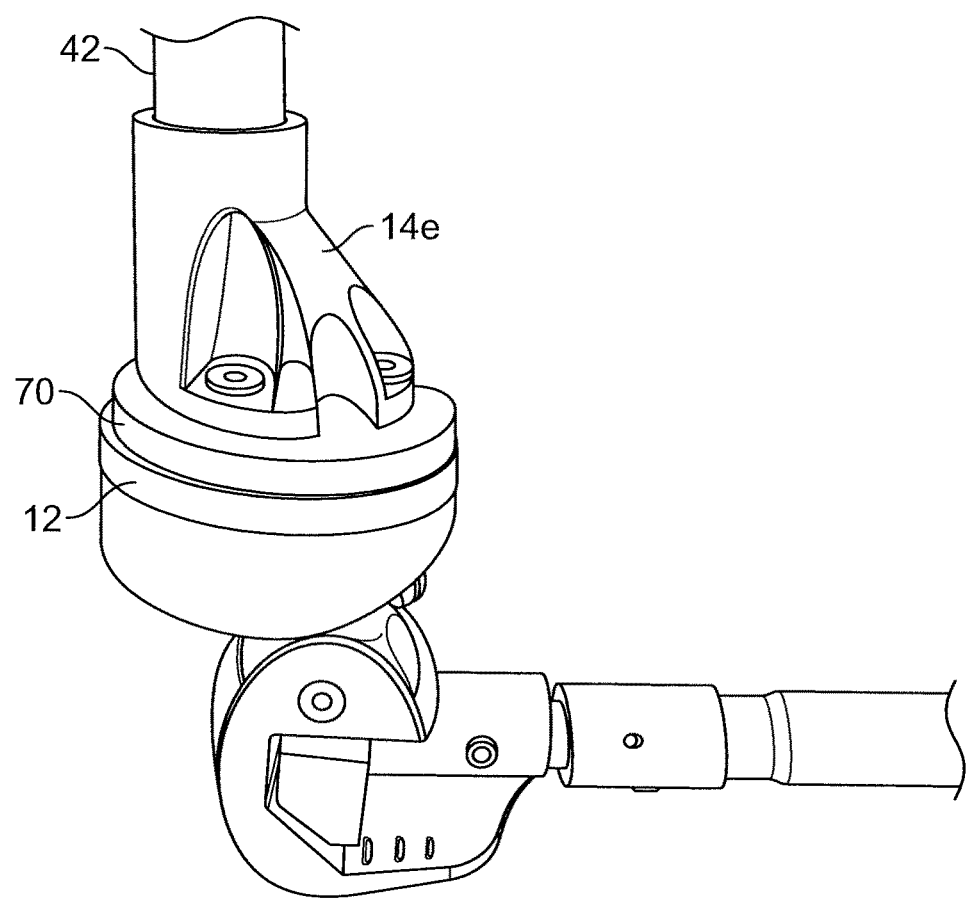
FIG. 22 illustrates the knee prosthesis kit including a wedge in a total knee replacement.
Figure 23:
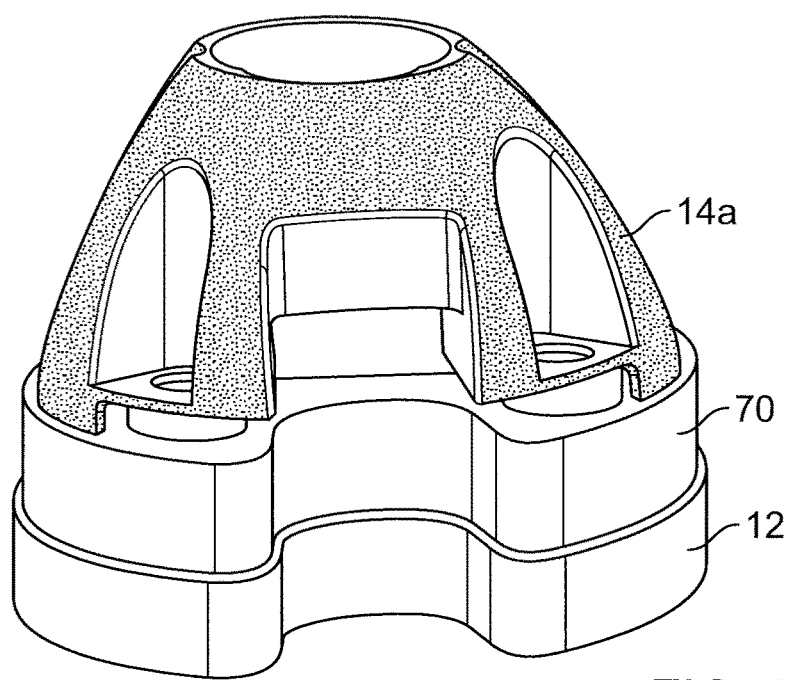
FIG. 23 illustrates the knee prosthesis kit including the wedge.

Referring to FIGS. 22 and 23, the kit 10 can further include one or more wedges 70 that can be positioned between the implant 12 and the augment 14 to raise the joint line. The kit 10 can include the coupler and the one or more wedges.

Figure 24A:
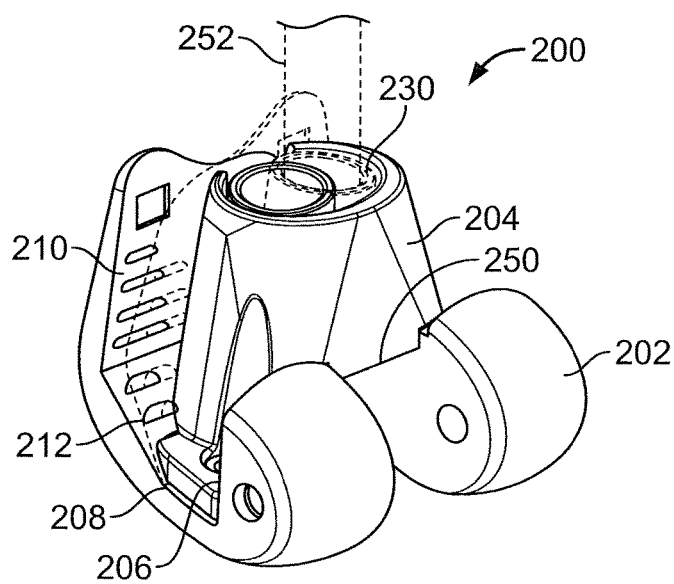
FIG. 24A is an isometric view of a knee prosthesis kit including a femoral implant and an augment.
Figure 24B:
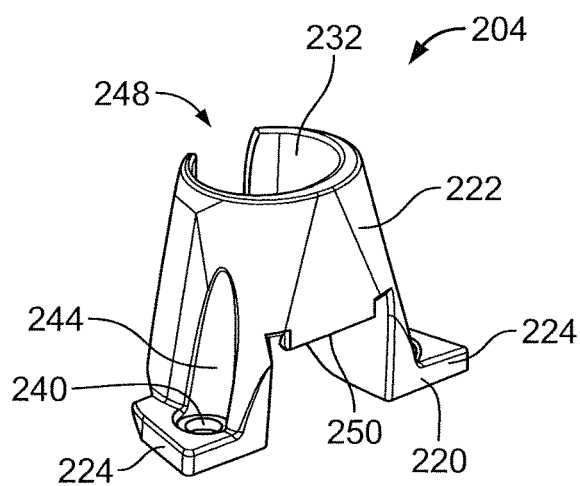
FIG. 24B is an isometric view of the augment of FIG. 24A.

Rather than a tibial plate, the implant 12 can be a femoral implant 202 (FIGS. 24A and 24B). A kit 200 for the femoral side includes the femoral implant 202 and an augment 204. The femoral implant 202 has an inner surface in the shape of a box cut having a posterior surface 206, a distal surface 208, and an anterior surface 210 joined to distal surface 208 by an angled surface 212. The augment 204 is sized to be received between the posterior and anterior surfaces 206, 210.

The augment 204 includes a base 220 and a cone-shaped portion 222. The base 220 includes two feet 224 sized to fit against distal surface 208 of the implant 202 between the posterior surface 206 and the angled surface 212, and within the profile of the distal surface 208 such that the feet 224 do not overhang the implant 202. The implant 202 includes a stem 230 and the cone-shaped portion 222 of the augment 204 and the augment base 220 define a bore 232 sized to receive the implant stem 230. The bore 232 is large enough to be able to receive the stem 230 of either a right femoral implant or a left femoral implant (FIG. 24A illustrates overlayed right and left femoral implants).

Figure 24C:
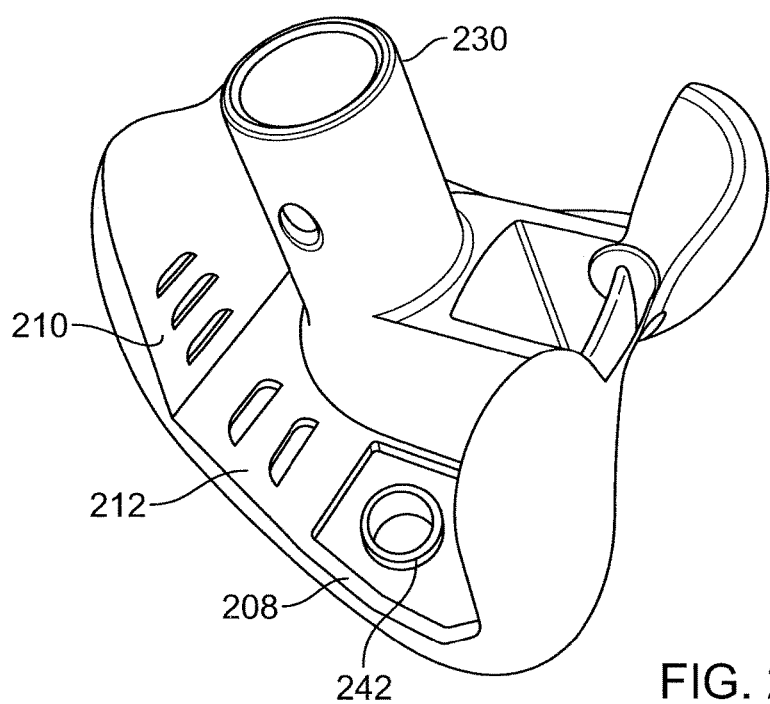
FIG. 24C is an isometric view of the femoral implant.
Figure 25A:
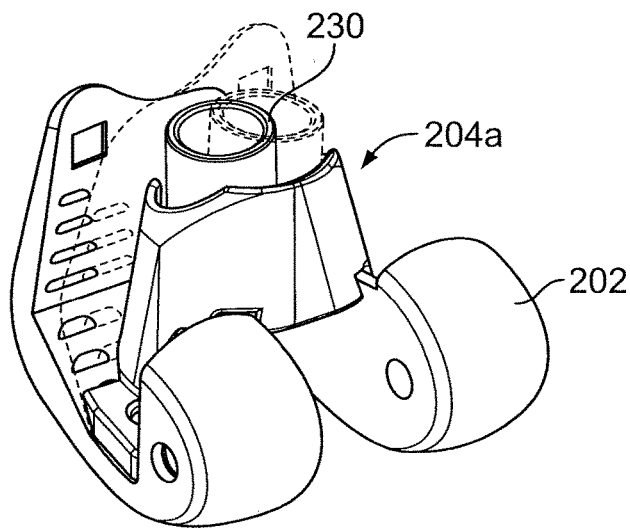
Figure 25B:
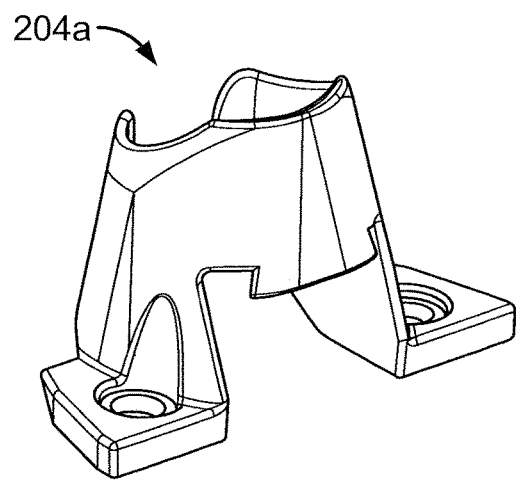
Figure 26A:
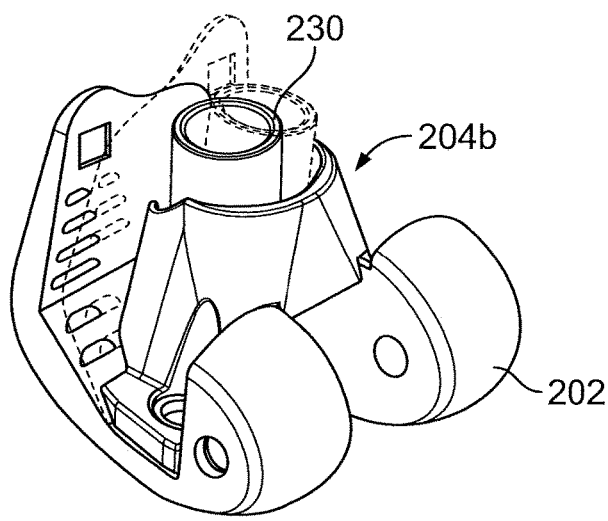
Figure 26B:
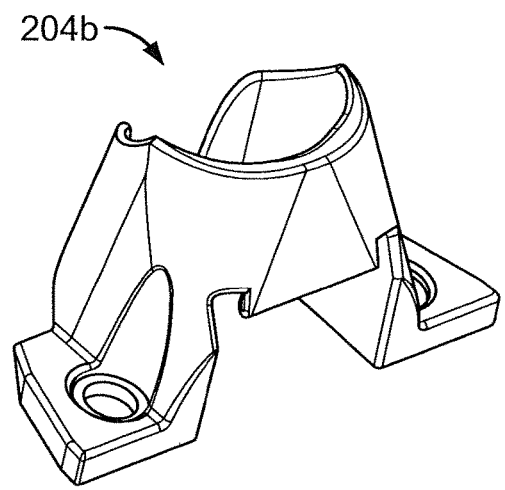

The augment base 220 has two openings 240 for receiving fasteners, and the implant 202 defines two openings 242 aligned with openings 240 for receiving fasteners (FIG. 24C, only one opening 242 is shown). The openings 242 do not extend all the way through the implant 202 such that the fasteners do not extend into the joint space. The cone-shaped portion 222 has slots 244 aligned with the augment base openings 242 that provide clearance for the fasteners.

As with the augment 14 discussed above, the cone-shaped portion 222 of the augment 204 is designed to optimize fixation of the implant 202, especially in the case of revision surgeries and/or oncology procedures, to improve fixation of the metaphyseal junction. In revision and primary procedures where the bone quality and ligamentous attachments are compromised, the cone-shaped portion 222 provides additional implant stability by filling the void left by bone deformities thus aiding in ensuring adequate fixation of the implant to the femur, promoting good function of the implant, and improving the rotational stability of the femur.

As illustrated in FIGS. 25A-26B, alternative augments 204a and 204b can be sized such that the stem 230 of the implant 202 extends beyond the augment bore 232 to facilitate attachment of further components, for example, a standard and/or offset coupler and an intramedullary rod 252, as discussed above, to the stem 230 of the implant 202. The kit 200 can also include one or more wedges, as discussed above. The augments can vary in shape and length to accommodate different bone deformities.

The augment 204 can include a slit 248 down the side facing the anterior surface 210 of the implant 202 for receipt by an implant of small size where there is not enough clearance between the anterior surface 210 and the stem 230 for placement of the augment 204 therebetween. The augment 204 can include a locking feature, for example, a tail 250 that snaps into the implant 202 to provide a friction fit between the knee augment 204 and the implant 202. Additional views of the implant 202 and augment 204 are shown in FIGS. 27A-27C, including the slit 248 and the tail 250.

A kit can include both the tibial components of kit 10 and the femoral components of kit 200.

A number of embodiments of the invention have been described. Nevertheless, it will be understood that various modifications may be made without departing from the spirit and scope of the invention. Accordingly, other embodiments are within the scope of the following claims.

What is claimed is:

1. A knee prosthesis kit, comprising:
    an implant including an implant base and a stem extending from the implant base, the implant base having a superior side and an inferior surface, and further including at least one planar wing extending from the stem and the inferior surface; and
    an augment including an augment base, the augment base having an implant surface and a bone contacting surface, the augment also including a cone-shaped portion extending distally from the augment base in a direction away from the bone contacting surface to a distal end of the cone-shaped portion, the cone-shaped portion having a cone-shaped outer surface, the augment base having at least two openings for receiving fasteners for securing the augment to the implant base, the cone-shaped portion and the augment base comprising a bore for receipt of the implant stem, the cone-shaped portion comprising at least two grooves extending distally from the augment base parallel to a direction of fastener insertion, wherein the at least two grooves are aligned with the at least two openings to provide clearance for the fasteners;
    wherein the inferior surface of the implant base is adapted to receive the implant surface of the augment, and the implant surface is engaged with the inferior surface when the augment is secured to the implant base; and
    wherein the augment further comprises a clearance space with a first portion in the augment base and a second portion in the cone-shaped portion, the first and second portions arranged to receive the at least one planar wing.

2. The knee prosthesis kit of claim 1 wherein the augment is sized relative to the implant such that when the augment is secured to the implant base, the stem extends out of the bore.

3. The knee prosthesis kit of claim 1 wherein the implant comprises a first implant or a second implant, the first implant being smaller than the second the implant, and wherein a first two of the openings are spaced apart to match the smaller size implant, and the other two of the openings are spaced apart a different amount from the first two openings to match the larger size implant.

4. The knee prosthesis kit of claim 1 wherein the implant base includes at least two openings for receiving fasteners, the implant base openings and the augment base openings being aligned when the augment is fastened to the implant.

5. The knee prosthesis kit of claim 4 wherein the implant base openings do not extend all the way through the implant base.

6. The knee prosthesis kit of claim 1 wherein the augment further comprises a locking feature configured to snap into the implant to provide a friction fit between the augment and the implant.

7. The knee prosthesis kit of claim 1 wherein an outer surface of at least the cone-shaped portion is sintered.

8. The knee prosthesis kit of claim 1 wherein the augment includes a cylindrical portion extending from the cone-shaped portion.

9. The knee prosthesis kit of claim 1 further comprising an offset coupler including a mating portion for receipt in a bore of the implant stem and a cone-shaped portion extending from the mating portion, the cone-shaped portion of the offset coupler defining a bore for receipt of an intramedullary rod, a central axis of the bore of the offset coupler being offset from a central axis of the mating portion.

10. The knee prosthesis kit of claim 9 wherein the offset coupler is configured to be secured in the bore of the implant stem by a taper lock.

11. The knee prosthesis kit of claim 9 further comprising the intramedullary rod.

12. The knee prosthesis kit of claim 11 wherein the offset coupler bore is configured to secure the intramedullary rod by a taper lock.

13. The knee prosthesis kit of claim 1 wherein the implant comprises a tibial implant.

14. The knee prosthesis kit of claim 1 wherein the implant comprises a femoral implant.

15. The knee prosthesis kit of claim 1, wherein the cone-shaped portion is fixed to the base when the augment is detached from the implant.

16. The knee prosthesis kit of claim 1, wherein the clearance space extends medially or laterally.

17. The knee prosthesis kit of claim 1, wherein the augment is configured to secure the augment base and the cone-shaped portion to the implant by receiving fasteners in the at least two openings in the augment base.

18. The knee prosthesis kit of claim 1, wherein the augment base is configured to connect with the implant in a manner that secures the cone-shaped portion to the implant.

19. The knee prosthesis kit of claim 18, wherein the augment is configured to be secured to the implant without the cone-shaped portion engaging the stem of the implant.

20. The knee prosthesis kit of claim 1, wherein the bore is sized to maintain a space between the stem of the implant and the cone-shaped portion of the augment when the augment is secured to the implant with the stem received in the bore.

21. The knee prosthesis kit of claim 1, wherein the wings and the stem are integrally connected to the implant base, wherein the bore of the augment extends from an opening in the base through the cone-shaped portion to an opening in the cone-shaped portion.

22. The knee prosthesis kit of claim 1, wherein the bore has an axis, the clearance space is defined through the base in a direction along the axis, and the clearance space is defined through the cone-shaped portion in a direction transverse to the axis.

23. The knee prosthesis kit of claim 1, wherein the clearance space extends through a portion of the augment that transitions from the augment base to the cone-shaped portion.

24. The knee prosthesis kit of claim 1, wherein:
the bore is sized to maintain a space between the stem of the implant and the cone-shaped portion of the augment when the augment is secured to the implant with the stem received in the bore; and
the cone-shaped portion extends distally from the implant base to a distal end of the cone-shaped portion, and wherein the cone-shaped portion has a region located distal to the clearance spaces that encircles the bore.

25. The knee prosthesis kit of claim 1, wherein the at least two grooves extend distally beyond an end of the second portion of the clearance space.

26. The knee prosthesis kit of claim 1, wherein the at least two grooves taper inwardly as the at least two grooves extend distally.

27. The knee prosthesis kit of claim 1, wherein the direction of fastener insertion is transverse to the augment base.

28. The knee prosthesis kit of claim 1, wherein the at least two grooves are separated from the bore by a wall of the cone-shaped portion.

29. A knee augment, for use with an implant, the implant having a bone contacting surface and an opposite surface, the knee augment comprising:
a base having at least one planar portion for engaging the implant and having at least two openings for receiving fasteners for securing the knee augment to the implant, the at least two openings are structured to receive the fasteners such that the fasteners extend in a direction transverse to the base; and
a cone-shaped portion extending distally from the base in a direction away from the bone contacting surface to a distal end of the cone-shaped portion, the cone-shaped portion having a cone-shaped outer surface, the cone-shaped portion and the base defining a bore for receipt of a stem of the implant, the cone-shaped portion comprising at least two grooves extending from the base in the direction transverse to the base, wherein each groove is aligned with a corresponding one of the at least two openings and provides clearance for a corresponding one of the fasteners;
wherein the base and the cone-shaped portion comprise clearance openings arranged to receive fin-like wings extending from the stem of the implant; and
wherein the clearance openings extend through a portion of the base and the clearance openings extend through the cone-shaped outer surface of the cone-shaped portion.

30. The knee augment of claim 29 wherein a first two of the openings are spaced apart to match a smaller size implant, and the other two of the openings are spaced apart a different amount from the first two openings to match a larger size implant.

31. The knee augment of claim 29 further comprising a locking feature configured to snap into the implant to provide a friction fit between the knee augment and the implant.

32. The knee augment of claim 29 further comprising a cylindrical portion extending from the cone-shaped portion, the cylindrical portion being integrally connected to the cone-shaped portion.

33. A knee prosthesis kit, comprising:
  an implant including an implant base, the implant base having a bone contacting side and an opposite side, and a stem extending from the implant base; and
  an augment including an augment base and a cone-shaped portion extending from the augment base, the cone-shaped portion having a cone-shaped outer surface, the augment base having at least two openings for receiving fasteners for securing the augment to the implant base, the cone-shaped portion and the augment base defining a bore for receipt of the implant stem, the augment further comprises a clearance space with a first portion in the augment base and a second portion in the cone-shaped portion, the first and second portions arranged to receive at least one planar wing of the implant, wherein the augment includes a cylindrical portion extending from a distal end of the cone-shaped portion, the bore extending through the cylindrical portion for receipt of the implant stem in the cylindrical portion; and wherein the cone-shaped portion comprises at least two grooves extending from the augment base parallel to a direction in which the fasteners extend when received in the at least two openings, and wherein the at least two grooves are aligned with the at least two openings and provide clearance for the fasteners.

34. The knee prosthesis kit of claim 33 wherein the bore extends entirely through the augment and the cone-shaped portion is integrally connected to the augment base.

35. The knee prosthesis kit of claim 33, wherein the cylindrical portion is integrally connected to the augment, and the bore extends entirely through the cylindrical portion.

* * * * *